United States Patent
Divi et al.

(10) Patent No.: US 8,664,443 B2
(45) Date of Patent: Mar. 4, 2014

(54) PROCESS FOR THE PREPARATION OF (1S, 3S, 5S)-2-[2(S)-2-AMINO-2-(3-HYDROXY-1-ADAMANTAN-1-YL) ACETYL]-2-AZABICYCLO [3.1.0] HEXANE-3-CARBONITRILE

(75) Inventors: Murali Krishna Prasad Divi, Hyderabad (IN); Gundu Rao Padakandla, Hyderabad (IN); Nageswara Rao Bolneni, Hyderabad (IN); Gopinarayana Bodala, Hyderabad (IN)

(73) Assignee: Divi's Laboratories Ltd. (IN)

( * ) Notice: Subject to any disclaimer, the term of this patent is extended or adjusted under 35 U.S.C. 154(b) by 0 days.

(21) Appl. No.: 13/602,956

(22) Filed: Sep. 4, 2012

(65) Prior Publication Data

US 2013/0317235 A1 Nov. 28, 2013

(30) Foreign Application Priority Data

May 23, 2012 (IN) ............................ 2065/CHE/2012

(51) Int. Cl.
*C07C 211/03* (2006.01)
*C07D 209/52* (2006.01)

(52) U.S. Cl.
USPC ........................................ 564/305; 548/452

(58) Field of Classification Search
USPC ........................................ 548/452; 564/305
See application file for complete search history.

(56) References Cited

U.S. PATENT DOCUMENTS

| | | | |
|---|---|---|---|
| 6,395,767 B2 | 5/2002 | Robl | |
| 7,186,846 B2 | 3/2007 | Sharma et al. | |
| 7,214,702 B2 | 5/2007 | Sharma | |
| 7,420,079 B2 | 9/2008 | Vu et al. | |
| 7,705,033 B2 | 4/2010 | Vu et al. | |
| 2008/0300251 A1 | 12/2008 | Sattigeri et al. | |
| 2010/0274025 A1 | 10/2010 | Vu et al. | |

OTHER PUBLICATIONS

Hiroshi Fukushima, et al. Synthesis and Structure-Activity Relationships of Potent 1-(2-Substituted-aminoacetyl)-4-fluoro-2-cyanopyrrolidine Dipeptidyl Peptidase IV Inhibitors, Chem. Pharm. Bull. 56(8)1110-1117 (2008).
Scott A. Savage, et al. Preparation of Saxagliptin, a Novel DPP-IV Inhibitor, Organic process Research & Development 2009, 13, 1169-1176.
G. Scott Jones, et al. Kinetic and Mechanistic Insight into the Thermodynamic Degradation of Saxagliptin, The Journal of Organic Chemistry, 2011, 76, 10332-10337.

*Primary Examiner* — Shawquia Young
(74) *Attorney, Agent, or Firm* — Caesar, Rivise, Bernstein, Cohen & Pokotilow, Ltd.

(57) ABSTRACT

The present invention relates to an improved process for the preparation of (1S,3S,5S)-2-[2(S)-2-amino-2-(3-hydroxy-1-adamantan-1-yl)acetyl]-2-azabicyclo[3.1.0]hexane-3-carbonitrile and its intermediates.

8 Claims, No Drawings

PROCESS FOR THE PREPARATION OF (1S, 3S, 5S)-2-[2(S)-2-AMINO-2-(3-HYDROXY-1-ADAMANTAN-1-YL) ACETYL]-2-AZABICYCLO [3.1.0] HEXANE-3-CARBONITRILE

CROSS-REFERENCE TO RELATED APPLICATION

This application claims priority from India Application 2065/CHE/2012, filed May 23, 2012, entitled A PROCESS FOR THE PREPARATION OF (1S,3S,5S)-2-[2(S)-2-AMINO-2-(3-HYDROXY-1-ADAMANTAN-1-YL) ACETYL]-2-AZABICYCLO[3.1.0]HEXANE-3-CARBONITRILE of which the following is a specification, which application is assigned to the same assignee as this application and whose disclosure is incorporated by reference herein.

FIELD OF INVENTION

The present invention relates to an improved process for the preparation of (1S,3S,5S)-2-[2(S)-2-amino-2-(3-hydroxy-1-adamantan-1-yl) acetyl]-2-azabicyclo[3.1.0]hexane-3-carbonitrile and its intermediates.

BACKGROUND OF THE INVENTION

Saxagliptin, (1S,3S,5S)-2-[2(S)-2-amino-2-(3-hydroxy-1-adamantan-1-yl)acetyl]-2-azabicyclo[3.1.0]hexane-3-carbonitrile of Formula I or its hydrochloride salt of Formula-II is an orally active reversible dipeptidyl peptidase-4 (DPP-4) inhibitor, which is a therapeutic agent for treatment of type-2 diabetes mellitus, obesity or related diseases and is disclosed in U.S. Pat. No. 6,395,767 example 60.

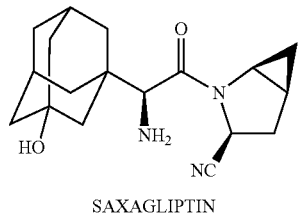

SAXAGLIPTIN

Formula-I

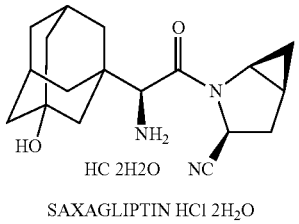

SAXAGLIPTIN HCl 2H₂O

Formula-II

Saxagliptin is marketed under the trade name ONGLYZA® by Bristol-Myers Squibb.

Saxagliptin, its hydrochloride and trifluoro acetate salts are disclosed in U.S. Pat. No. 6,395,767B2. U.S. Pat. No. 7,420,079B2 and its continuation US Pat. No. 2010/0274025 A1 disclosed process for preparing Saxagliptin and its hydrochloride, trifluoro acetate and benzoate salts, as well as Saxagliptin monohydrate. U.S. Pat. No. 7,705,033 B2 disclosed process for preparing Saxagliptin monohydrate. U.S. Pat. No. 7,214,702 B2 also disclosed similar processes for the preparation of Saxagliptin and its hydrochloride salt.

The essential steps of the processes disclosed in all the above said patents are summarized as Scheme-I below.

Scheme-I

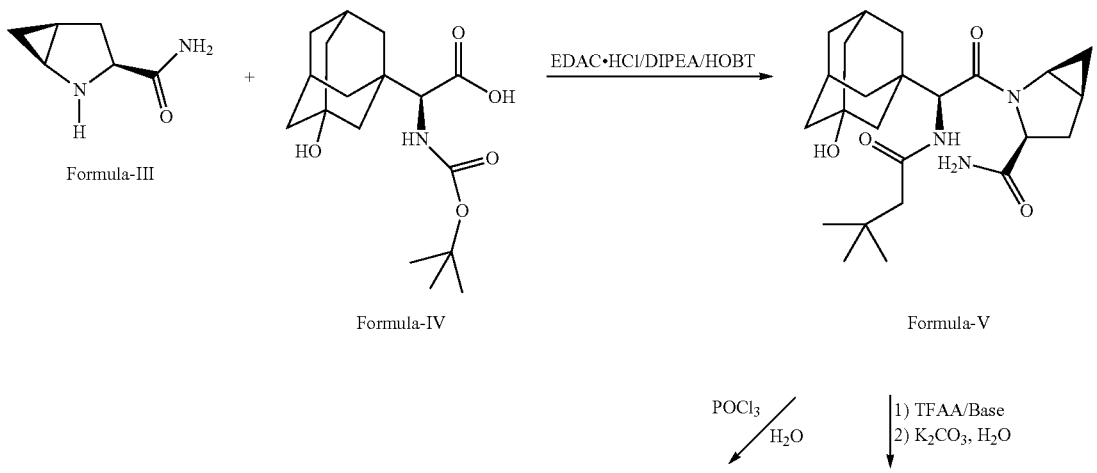

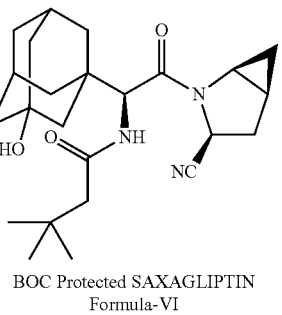

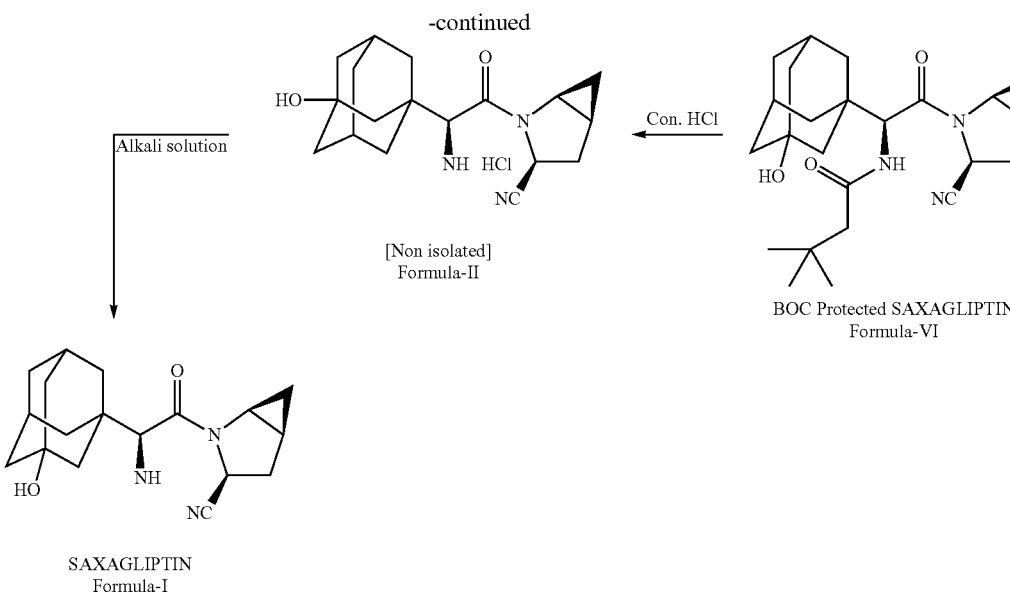

Tertiary butyloxy carbonyl (BOC) protected Saxagliptin of formula-VI was deprotected with aqueous hydrochloric acid, converted into Saxagliptin hydrochloride salt of formula-II, which was further treated with an alkali solution and extracted with an organic solvent to obtain the free base (1S,3S,5S)-2-[2(S)-2-amino-2-(3-hydroxy-1-adamantan-1-yl)acetyl]-2-azabicyclo[3.1.0]hexane-3-carbonitrile of formula-I.

The above process suffers from the drawback that the tertiary-butyloxy carbonyl (BOC) protecting group was sensitive towards acidic experimental conditions during the condensation of compounds of formula-III and IV and transformation of the amide group to cyano group subsequently. Without this protection, the amino group is available for interaction with the cyano group leading to undesirable products as explained later.

U.S. Pat. No. 7,186,846B2 disclosed a process for the preparation of Saxagliptin base through the reductive cleavage of a protected Saxagliptin (protected with trifluoro acetyl group) as shown in Scheme-II below.

Scheme-II

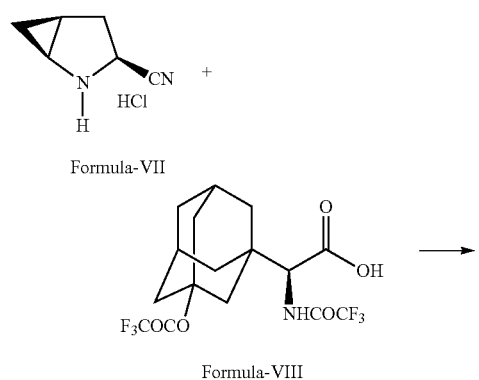

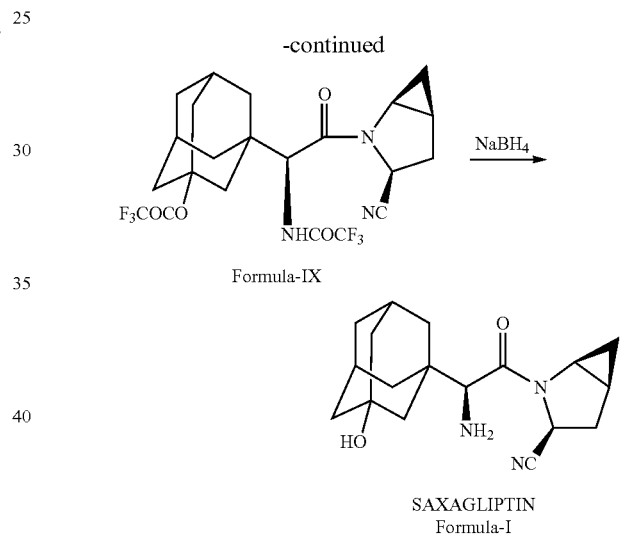

Hiroshi Fukushima et al (Chem. Pharm. Bull., 56(8), 1110-1117, 2008) reported the instability of 2-cyano fluoro pyrrolidine derivatives at pH 6-8 due to intramolecular attachment of basic nitrogen to the cyano group which leads to the formation of cyclic amidine, with subsequent further transformation into diketopiperazine derivatives. Saxagliptin can also be viewed as a derivative of 2-cyano pyrrolidine which may undergo formation of the cyclic amidine through intramolecular cyclisation.

The acid salts of Saxagliptin are generally stable in solution. However, isolation of the free base (1S,3S,5S)-2-[2(S)-2-amino-2-(3-hydroxy-1-adamantan-1-yl)acetyl]-2-azabicyclo[3.1.0]hexane-3-carbonitrile of formula-I from its hydrochloride salt of formula-II is difficult. Scott Jones et al (OPRD 13, 1169-1176, 2009) have shown (Scheme-III below) that Saxagliptin base underwent intramolecular cyclisation to form cyclic amidine of formula-X under alkaline conditions.

Scheme-III

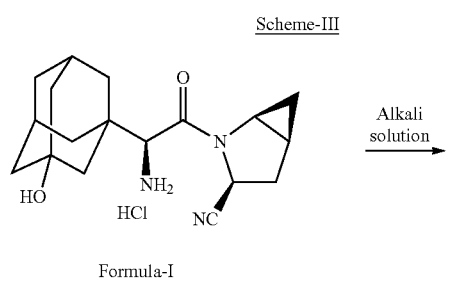

Formula-I

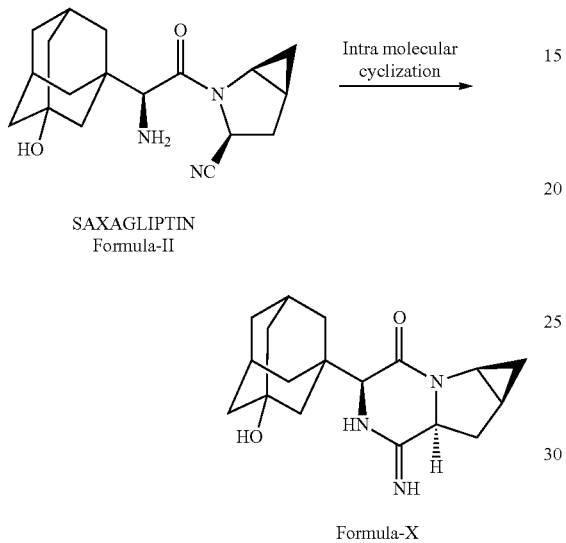

SAXAGLIPTIN
Formula-II

Further Scott Jones et al (JOC, 76, 10332-10337, 2011) reported that, "during the development of Saxagliptin manufacturing process, it was observed that the rate of cyclisation increases monotonically with pH". Since the resultant cyclic amidine [CA] of formula-VIII is not therapeutically active; its formation is not desirable.

All the methods disclosed in the literature and patents employ treatment of Saxagliptin hydrochloride with an alkali solution to prepare Saxagliptin base, which process is not preferable because it leads to the formation of the cyclic amidine impurity under the basic pH conditions.

Therefore there is a need for an improved, industrially applicable process to overcome the above problems.

The present invention provides new methods and compounds for use in the process for making of Saxagliptin free base of formula-I.

SUMMARY OF THE INVENTION

Because of the drawbacks associated in the conversion of the Saxagliptin hydrochloride into Saxagliptin free base such as formation of cyclic amidine impurity under alkaline conditions, the present inventors investigated other possible protecting groups.

After considerable experimentation with various protecting groups, it was found that the benzyloxy carbonyl group (CBZ) is a preferable choice. The selected benzyloxy carbonyl group (CBZ) is quite stable under the reaction conditions. Our studies showed that the benzyloxy carbonyl group of CBZ-protected Saxagliptin can be easily cleaved under mild hydrogenation in neutral medium to yield Saxagliptin free base of formula-I and formation of the cyclic amidine impurity was minimized to the specified limit of <0.1%, as shown below in Scheme-IV. Further the base could be directly converted to Saxagliptin HCl or other salts if desired.

A simple and convenient approach has been developed for the direct formation of the Saxagliptin free base of formula-I using CBZ protected Saxagliptin without the intermediate hydrochloride salt as in prior art processes.

Scheme-IV

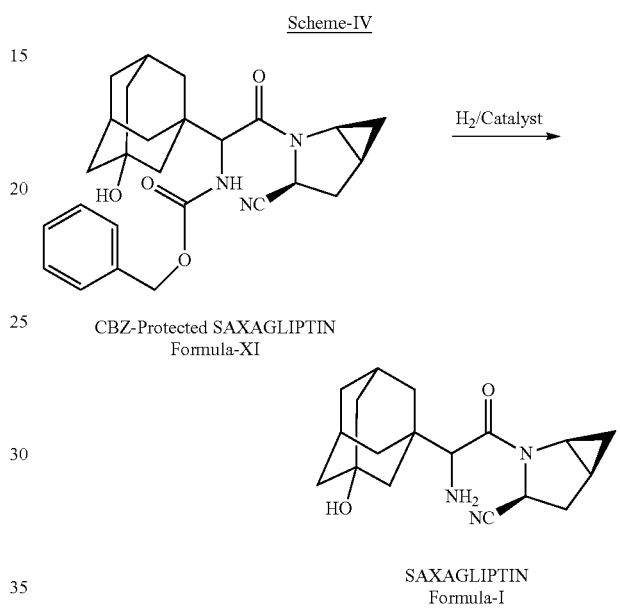

In accordance with the present invention a process is provided for preparing Saxagliptin free base of formula-I which include the steps of a) providing a compound of formula-XIV

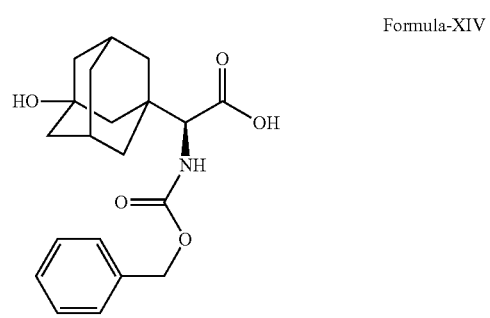 [SMILES: O=C(N[C@H](C(=O)O)C12CC3CC(CC(O)(C3)C1)C2)OCc1ccccc1]

b) coupling the compound of formula-XIV with a compound of formula-XIII

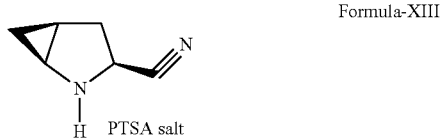

to form the compound of formula-XI

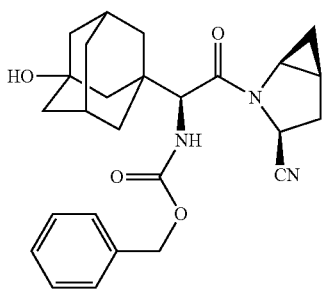
Formula-XI c) deprotecting the compound of formula-XI using hydrogen source to give compound of formula-I

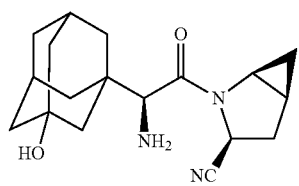
Formula-I

Alternately in accordance with the present invention, a process is provided for preparing compound of formula-I using compound of formula-III, which includes the steps of
a) Coupling of compound of formula-XIV with compound of formula-III

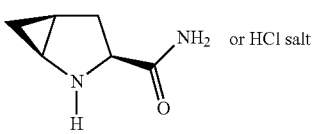
Formula-III to give compound of formula-XV

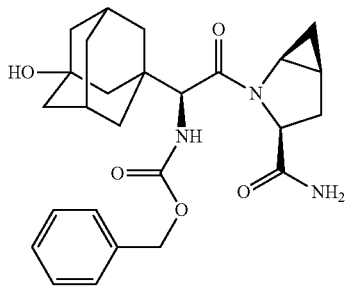
Formula-XV b) dehydration followed by hydrolysis of the formula-XV to give compound of formula-XI

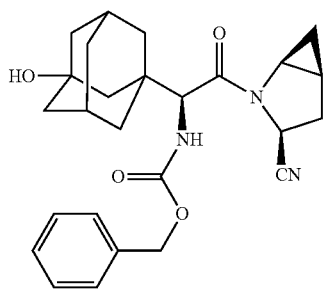
Formula-XI c) deprotecting the compound of formula-XI using hydrogen source to give compound of formula-I

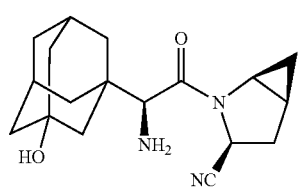
Formula-I

The process has the following advantages over the earlier processes: amenable for large scale industrial production, direct formation of Saxagliptin free base from CBZ-protected Saxagliptin of Formula-XI and minimizes the formation of the cyclic amidine of formula-X by employing mild conditions.

The invention is also useful to prepare Saxagliptin hydrates and its salts, as for example Saxagliptin mono hydrate, Saxagliptin HCl and its hydrates.

DETAILED DESCRIPTION OF THE INVENTION

The invention relates to direct synthesis of Saxagliptin free base of formula-I from benzyl N-[(1S)-2-[(1S,3S,5S)-3-cyano-2-azabicyclo[3.1.0]hexan-2-yl]-1-(3-hydroxyadamantan-1-yl)-2-oxo-ethyl]carbamate of formula-XI, which is depicted by the following reaction Scheme-V. The base so obtained may be optionally converted to its hydrate or hydrochloride salt and its hydrate.

Scheme-V

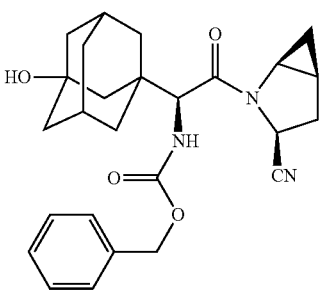

CBZ protected Saxagliptin
Formula-XI

↓ Hydrogen

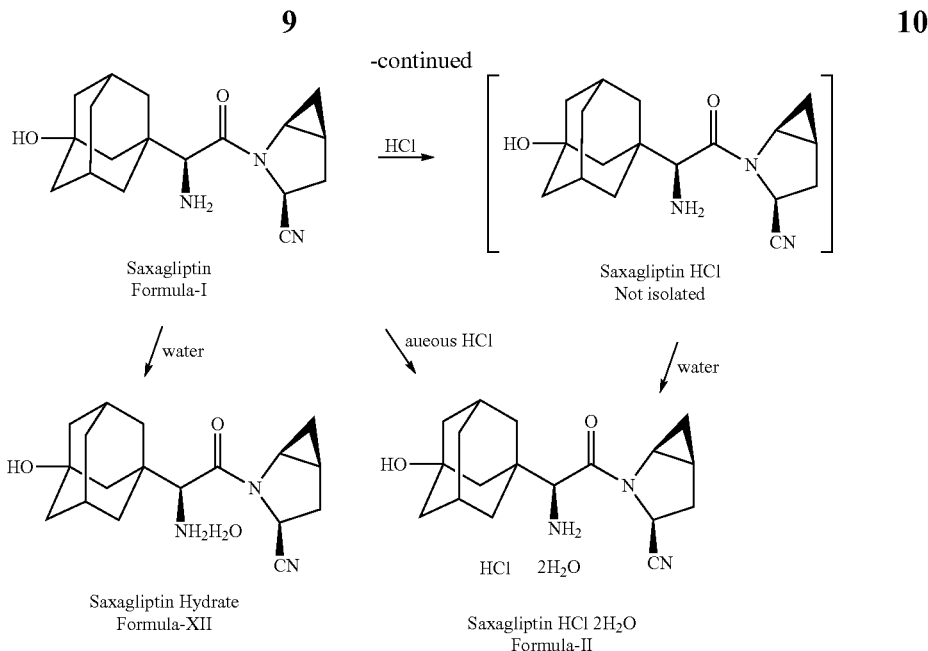

In one embodiment the present invention refers to the process for preparing Saxagliptin of formula-I comprising deprotection of the benzyloxy carbonyl group of benzyl N-[(1S)-2-[(1S,3S,5S)-3-cyano-2-azabicyclo[3.1.0]hexan-2-yl]-1-(3-hydroxyadamantan-1-yl)-2-oxo-ethyl]carbamate of formula-XI by dissolving it in a suitable solvent or mixtures of solvents, treating with a hydrogen source in presence of a metal catalyst to yield Saxagliptin free base of formula-I.

The reaction is carried out with solvents which may include but are not limited to methanol, ethanol, isopropyl alcohol, butanol, acetonitrile, tetrahydrofuran, ethyl acetate, acetic acid or water, preferably in methanol or more preferably in acetonitrile.

The reaction is carried out with hydrogen source, which may include but are not limited to hydrogen gas, formic acid, ammonium formate, ammonium acetate or ammonium chloride preferably hydrogen gas.

The hydrogen gas used may be atmosphere of hydrogen gas, bubbling of hydrogen gas or hydrogen gas under pressure, preferably bubbling of hydrogen gas.

The reaction is carried out at 0° C. to 50° C. temp, preferably at 15-30° C. temperature.

The reaction is carried out in presence of a metal catalyst such as palladium on carbon (Pd/C).

The duration of the reaction is about 1 to 6 hr, preferably 2 hrs.

In another embodiment the present invention refers to deprotection of benzyl N-[(1S)-2-[(1S,3S,5S)-3-cyano-2-azabicyclo[3.1.0]hexan-2-yl]-1-(3-hydroxyadamantan-1-yl)-2-oxo ethyl]carbamate of Formula-XI to give the [(1S,3S,5S)-2-[2(S)-2-amino-2-(3-hydroxy-1-adamantan-1-yl)acetyl]-2-azabicyclo[3.1.0]hexane-3-carbonitrile] monohydrate of Formula-XII.

The process for preparing Saxagliptin monohydrate of formula-XII comprises, deprotection of the benzyloxy carbonyl group of benzyl N-[(1S)-2-[(1S,3S,5S)-3-cyano-2-azabicyclo[3.1.0]hexan-2-yl]-1-(3-hydroxyadamantan-1-yl)-2-oxoethyl]carbamate of Formula-XI by dissolving in a suitable solvent or mixtures of solvents, treating with a hydrogen source and in presence of the metal catalyst to yield Saxagliptin base of formula-I. The obtained Saxagliptin base is dissolved in a suitable solvent or mixtures of solvents, treated with one equivalent of water to yield Saxagliptin monohydrate of formula-XII.

In yet another embodiment the invention encompasses the process for preparing Saxagliptin salt from Saxagliptin base of formula-I.

The process for preparing Saxagliptin salt from Saxagliptin base comprises, dissolving Saxagliptin base in a suitable solvent such as ethyl acetate, diisopropyl ether, methyl tertiary butyl ether, acetonitrile, butanol, isopropyl alcohol, ethanol, methanol, tetrahydrofuran or mixtures there of, treating with one equivalent of a mineral acid or organic acid at a temperature of about 0-30° C. for a period of about 30 min to 12 hr to obtain a suspension of Saxagliptin salt. Saxagliptin salt can be recovered from the suspension, by filtering and drying.

The process for preparing hydrates of Saxagliptin salt comprises, treating Saxagliptin salt with water in a suitable solvent such as ethyl acetate, diisopropyl ether, methyl tertiary butyl ether, acetonitrile, butanol, isopropyl alcohol, ethanol, methanol, tetrahydrofuran or mixtures there of, at a temperature of about 0-30° C. for a period of about 30 min to 12 hr to obtain a suspension of hydrates of Saxagliptin salt. Hydrates of Saxagliptin salt can be recovered from the suspension, by filtering.

The mineral acid for preparing Saxagliptin salt from Saxagliptin base herein includes hydrogen chloride, hydrogen bromide or phosphoric acid preferably aqueous hydrochloric acid.

The organic acid for preparing Saxagliptin salt from Saxagliptin base herein includes trifluoro acetic acid, methanesulfonic acid, tartaric acid, oxalic acid, fumaric acid, salicylic acid, maleic acid, and para toluenesulfonic acid.

The salt formation reaction can also be carried out by any other acid known to a person skilled in the art.

Benzyl N-[(1S)-2-[(1S,3S,5S)-3-cyano-2-azabicyclo[3.1.0]hexan-2-yl]-1-(3-hydroxyadamantan-1-yl)-2-oxo-ethyl]carbamate of Formula-XI can be prepared as depicted in Scheme-VI.

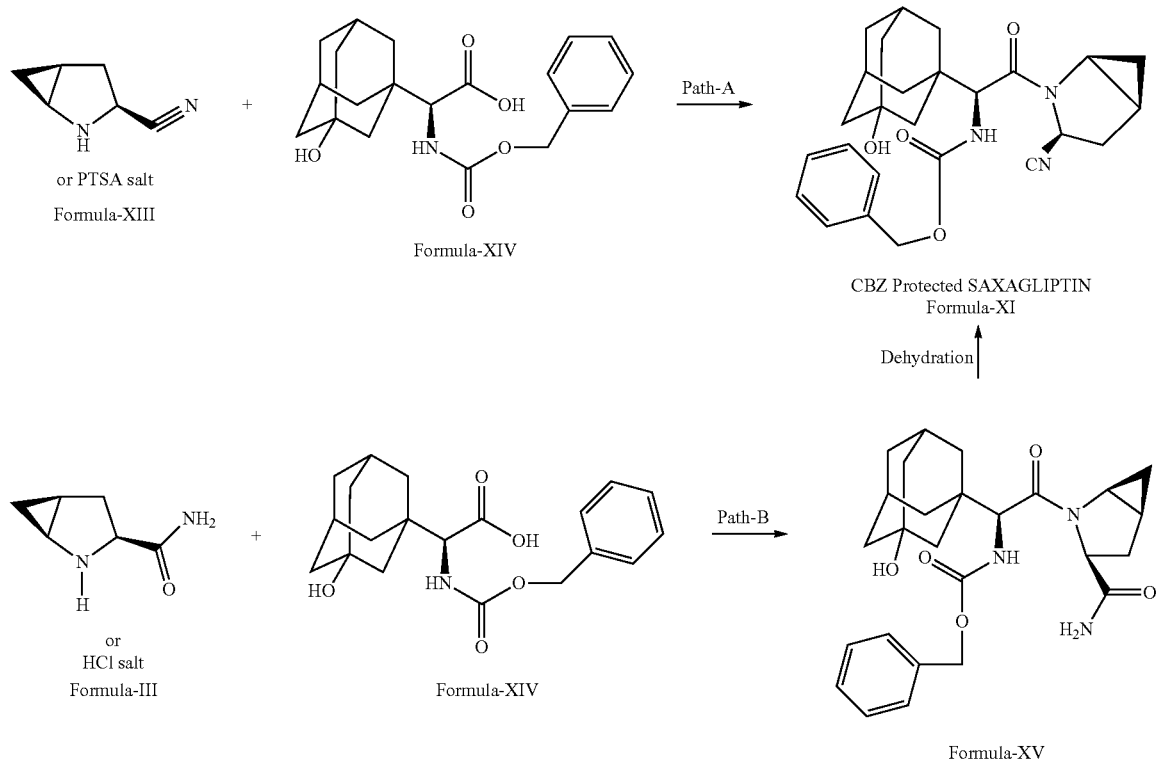

Scheme-VI

CBZ Protected SAXAGLIPTIN
Formula-XI

Formula-XV

The compound of Formula-XI [CBZ-protected Saxagliptin] can be prepared following Scheme-VI.

Path A: (1S,3S,5S)-2-Azabicyclo[3.1.0]hexane-3-carbonitrile or its salts of formula-XIII can be coupled with (2S)-2-{[(benzyloxy)carbonyl]amino}-2-(3-hydroxyadamantan-1-yl)acetic acid of formula-XIV to give benzyl N-[(1S)-2-[(1S,3S,5S)-3-cyano-2-azabicyclo[3.1.0]hexan-2-yl]-1-(3-hydroxyadamantan-1-yl)-2-oxo-ethyl]carbamate of Formula-XI in a suitable solvent, for example, tetrahydrofuran, N,N-dimethyl formamide, 1,4-dioxane or ethyl acetate using a coupling agent, for example, 1,3-dicyclohexyl carbodiimide (DCC), 1-ethyl-3-(3'-dimethyl amino propyl)carbodiimide (EDAC), 1-propane phosphonic acid cyclic anhydride or N-[(dimethylamino)-1H-1,2,3-trizole[4,5-b]pyridylmethylene]-N-methylmethanaminium hexafluoro phosphate N-oxide (HATU) and optionally, a catalyst, for example, 1-hydroxybenzotriazole (HOBT) or 7-aza-hydroxylbenzotriazole (HOAt) and optionally, with a base, for example, N,N-dimethylamino pyridine (DMAP), triethylamine, N,N-diisopropylethylamine or N-methyl morpholine.

The coupling reaction of compound of Formula-XIII with compound of Formula-XIV can be carried out at a temperature of about 0° C. to 45° C. preferably at 20 to 25° C.

The reaction can also be carried out by any other method for amide bond formation known to a person skilled in the art.

Path B: Coupling reaction of (1S,3S,5S)-2-azabicyclo[3.1.0]hexane-3-carboxamide or its salts of Formula-III with (2S)-2-{[(benzyloxy)carbonyl]amino}-2-(3-hydroxyadamantan-1-yl)acetic acid of formula-XIV to give benzyl N-[(1S)-2-[(1S,3S,5S)-3-carbamoyl-2-azabicyclo[3.1.0]hexan-2-yl]-1-(3-hydroxyadamantan-1-yl)-2-oxo-ethyl]carbamate of formula-XV, can be carried out in a suitable solvent, for example, tetrahydrofuran, N,N-dimethyl formamide, 1,4-dioxane or ethyl acetate using a coupling agent for example, 1,3-dicyclohexyl carbodiimide (DCC), 1-ethyl-3-(3'-dimethylaminoporpyl)carbodiimide (EDAC), 1-propane phosphonic acid cyclic anhydride or N-[(dimethyl amino)-1H-1,2,3-triazolo[4,5-b]pyridylmethylene]-N-methyl methanaminium hexafluoro phosphate N-oxide (HATU) and optionally a catalyst, for example, 1-hydroxybenzotriazole (HOBT) or 7-aza-1-hydroxy benzotriazole (HOAt) and optionally, with a base, for example, N,N-dimethylamino pyridine (DMAP), triethylamine, N,N-diisopropyl ethyl amine, or N-methyl morpholine.

The coupling reaction can be carried out under inert atmosphere from 0° C. to 45° C. preferably at 20 to 25° C.

The coupling reaction can also be carried out by any other method for amide bond formation known to a person skilled in the art.

The [benzyl N-[(1S)-2-[(1S,3S,5S)-3-carbamoyl-2-azabicyclo[3.1.0]hexan-2-yl]-1-(3-hydroxyadamantan-1-yl)-2-oxo-ethyl]carbamate] of Formula-XV so obtained is subjected to dehydration by treating with an organic base such as pyridine, triethylamine, diisopropylethylamine or ethyl nicotinate and trifluoroacetic anhydride in a suitable solvent, for example, ethyl acetate, dichloromethane, chloroform or toluene and then to hydrolysis by cooling to from about 0° C. to about 10° C. and adding an alkali solution containing NaOH, KOH, LiOH, $K_2CO_3$ or $Na_2CO_3$ to form the benzyl N-[(1S)-2-[(1S,3S,5S)-3-cyano-2-azabicyclo[3.1.0]hexan-2-yl]-1-(3-hydroxyadamantan-1-yl)-2-oxo-ethyl]carbamate of Formula-XI.

The deprotection and hydrolysis reactions can also be carried out by any other method known to persons skilled in the art, including a one-pot approach.

The (2S)-2-{[(benzyloxy)carbonyl]amino}-2-(3-hydroxyadamantan-1-yl)acetic acid of formula-XIV can be prepared by reacting (2S)-2-amino-2-(3-hydroxyadamantan-1-yl)acetic acid or its salts with benzyl chloroformate in a suitable solvent like water in presence of a base like sodium hydroxide at a pH of between 7 and 10 and at a temperature of −10° C. to 35° C., preferably at 0° C.

The (1S,3S,5S)-2-azabicyclo[3.1.0]hexane-3-carbonitrile or its salts of formula-XIII may be prepared as per procedure given in US2008/0300251A1 (currently abandoned).

The (1S,3S,5S)-2-azabicyclo[3.1.0]hexane-3-carboxamide or its salts of Formula-III may be prepared as per procedure given in U.S. Pat. No. 7,420,079B2.

The invention is described in more detail in the following examples but is not limited to the conditions described. The reagents and solvents mentioned in examples are for illustration purpose only and may be replaced by other reagents and solvents known to those skilled in the art.

EXAMPLE-1

Preparation of benzyl N-[(1S)-2-[(1S,3S,5S)-3-carbamoyl-2-azabicyclo[3.1.0]hexan-2-yl]-1-(3-hydroxyadamantan-1-yl)-2-oxo ethyl]carbamate (formula-XV)

(2S)-2-{[(Benzyloxy)carbonyl]amino}-2-(3-hydroxyadamantan-1-yl)acetic acid of Formula-XIV (20 gm), 1-ethyl-3-(3-dimethyl aminoporpyl)carbodiimide (13.8 gm), (1S,3S, 5S)-2-azabicyclo[3.1.0]hexane-3-carboxamide of formula-III (14.8 gm) and 1-hydroxy benzotriazole (10.2 gm) were dissolved in N,N-dimethyl formamide (80 ml). The reaction mixture was cooled to about 20° C. Addition of N,N-diisopropylethylamine (15.8 gm) was then carried out for 15 min. The reaction mixture was stirred for 4 hrs and the solvent was distilled off. To the residue 2N HCl solution was added. Aqueous phase was extracted with ethyl acetate. Organic phase was washed with $NaHCO_3$ solution, dried and evaporated to yield 23.3 gms (90%) of title product. MP: 105-106° C., $H^1$NMR (300 MHz, CDCl3): 0.81 (dd, 1H), 0.96 (m, 1H), 1.46-1.82 (m, 12H), 1.93 (s, 1H), 2.2 (m, 3H), 2.45 (dd, 1H), 3.6 (m, 1H), 4.5-4.61 (dd, 1H), 4.76-4.86 (dd, 1H), 5.0 (s, 2H), 5.34 (d, 1H), 5.69 (s, 1H), 5.82-5.85 (dd, 1H), 6.83-6.89 (s, 1H), 7.31-7.35 (m, 5H).

EXAMPLE-2

Preparation of Benzyl N-[(1S)-2-[(1S,3S,5S)-3-cyano-2-azabicyclo[3.1.0]hexan-2-yl]-1-(3-hydroxyadamantan-1-yl)-2-oxo ethyl]carbamate (Formula-XI)

Trifluoro acetic anhydride (41.36 gm) was added to a solution of [benzyl N-[(1S)-2-[(1S,3S,5S)-3-carbamoyl-2-azabicyclo[3.1.0]hexan-2-yl]-1-(3-hydroxyadamantan-1-yl)-2-oxo-ethyl]carbamate of formula-XV (27 gm) and ethyl nicotinate (30.6 gm) in ethyl acetate at 0-5° C. After 6 hrs water was added to the reaction. Organic phase was washed with 2N HCl solution, dried and concentrated. The crude compound obtained was dissolved in methanol, hydrolyzed with aqueous potassium carbonate (112 gm of $K_2CO_3$ in 228 ml water) for 2 hrs at 25° C. Solvent was distilled off from the reaction mass and aqueous phase extracted with ethyl acetate. Organic phase was dried and evaporated and the solid obtained was purified in THF to yield 20.8 gm (80%) of the desired product. M.P: 148-150° C., HPLC Purity: 99.5% (A), $H^1$NMR (300 MHz, CDCl3): 1.06-1.09 (m, 2H), 1.45-1.9 (m, 12H), 2.25 (m, 2H), 2.33-2.38 (dd, 1H), 2.52-2.54 (m, 1H), 3.82-3.84 (dd, 1H), 4.5 (d, 1H), 4.99-5.04 (dd, 1H), 5.08 (s, 2H), 5.59-5.63 (d, 1H), 7.32-7.63 (m, 5H).

EXAMPLE-3

Preparation of Benzyl N-[(1S)-2-[(1S,3S,5S)-3-cyano-2-azabicyclo[3.1.0]hexan-2-yl]-1-(3-hydroxyadamantan-1-yl)-2-oxo ethyl]carbamate (Formula-XI)

(2S)-2-{[(Benzyloxy)carbonyl]amino}-2-(3-hydroxyadamantan-1-yl)acetic acid of formula-XIV (20 gm), (1S,3S, 5S)-2-azabicyclo[3.1.0]hexane-3-carbonitrile PTSA salt of Formula-XIII (16 gm), 1-ethyl-3-(3-dimethylaminoporpyl) carbodiimide (12 gm) and 1-hydroxy benzotriazole (1.2 gm) were dissolved in ethyl acetate (20 ml) and acetonitrile (40 ml). The reaction mixture was cooled to 20° C. Then addition of N,N-diisopropylethylamine (16 gm) was carried out for 15 min. The reaction mixture was stirred for 8 hrs and washed with 2N HCl solution. Organic phase was washed with $NaHCO_3$ solution, dried and evaporated to yield 19.8 gm (80%) of title product. MP: 105-106° C.

EXAMPLE-4

Preparation of Saxagliptin Mono Hydrate (Formula-XII)

To a solution of benzyl N-[(1S)-2-[(1S,3S,5S)-3-cyano-2-azabicyclo[3.1.0]hexan-2-yl]-1-(3-hydroxyadamantan-1-yl)-2-oxo-ethyl]carbamate (10 gm) (formula-IX) in acetonitrile, 5% Pd/C (50% wet, 1 gm) was added. Hydrogen gas was bubbled through the reaction mass for 4 hrs at 20-25° C. After the starting material was completely converted, the reaction mass was filtered and the filtrate evaporated to yield SAXAGLIPTIN free base of formula-I as a foamy solid. To the solid ethyl acetate (5 ml), 20 micro liters of water and n-hexane (20 ml) were added; the mixture stirred at 0-5° C. and filtered the white solid formed to yield 7.06 gm (95%) of SAXAGLIPTIN MONO HYDRATE. HPLC Purity: 99.7% (A) and the content of the impurity cyclic amidine: 0.07% (A), M.P: 105-108° C., $H^1$NMR (300 MHz, Methanol-d4): 0.83-1.06 (m, 2H), 1.36-1.7 (m, 12H), 1.79-1.88 (ddd, 1H), 2.19 (m, 2H), 2.23 (dd, 1H), 2.46-2.56 (ddd, 1H), 3.49 (s, 1H), 3.72-3.77 (ddd, 1H), 4.96-5.01 (dd, 1H).

EXAMPLE-5

Preparation of Saxagliptin Mono Hydrate (Formula-XII)

To a solution of benzyl N-[(1S)-2-[(1S,3S,5S)-3-cyano-2-azabicyclo[3.1.0]hexan-2-yl]-1-(3-hydroxyadamantan-1-yl)-2-oxo-ethyl]carbamate (10 gm) (formula-IX) in methanol 5% Pd/C (50% wet, 1 gm) was added. Hydrogen gas was bubbled through the reaction mass for 2 hrs at 20-25° C. After the starting material was completely converted, the reaction mass was filtered. The filtrate was evaporated to yield SAXAGLIPTIN free base of formula-I as a foamy solid. To the solid ethyl acetate (5 ml), 20 micro liters of water and n-hexane (20 ml) were added, stirred at 0-5° C. and filtered the white solid formed to yield 6.98 gm (94%) of SAXAGLIPTIN MONO HYDRATE. HPLC Purity: 99.5% (A) and the content of the impurity cyclic amidine: 0.09% (A), M.P: 105-108° C.

EXAMPLE-6

Preparation of Saxagliptin Dihydrate Mono Hydrochloride (Formula-II)

To a solution of benzyl N-[(1S)-2-[(1S,3S,5S)-3-cyano-2-azabicyclo[3.1.0]hexan-2-yl]-1-(3-hydroxyadamantan-1-yl)-2-oxo-ethyl]carbamate (10 gm) (formula-IX) in acetonitrile, 5% Pd/C (50% wet, 1 gm) was added. Hydrogen gas was bubbled through the reaction mass for 4 hrs at 20-25° C. After complete conversion of starting material, the reaction mass was filtered, the filtrate was evaporated to yield SAXAGLIPTIN free base of formula-I as a foamy solid. The solid was dissolved in ethyl acetate (50 ml) and concentrated hydrochloric acid (2.4 ml) was added at 5-10° C. The white solid formed was filtered to yield 7.8 gm (99%) of SAXAGLIPTIN dihydrate mono-hydrochloride M.P: 228-230° C., HPLC: 99.7% (A) and the content of the impurity cyclic amidine: 0.05% (A), H$^1$NMR (300 MHz, Methanol-d4): 0.87-1.13 (m, 2H), 1.48-1.7 (m, 12H), 1.89-1.96 (ddd, 1H), 2.19 (s, 1H), 2.22-2.28 (dd, 1H), 2.49 (ddd, 1H), 3.83-3.88 (ddd, 1H), 4.19 (s, 1H), 5.08-5.12 (dd, 1H).

EXAMPLE-7

Preparation of Saxagliptin Dihydrate Mono Hydrochloride (Formula-II)

To a solution of benzyl N-[(1S)-2-[(1S,3S,5S)-3-cyano-2-azabicyclo[3.1.0]hexan-2-yl]-1-(3-hydroxyadamantan-1-yl)-2-oxo-ethyl]carbamate (10 gm) of formula-IX in acetonitrile, 5% Pd/C (50% wet, 1 gm) was added. Hydrogen gas was bubbled through the reaction mass for 4 hrs at 20-25° C. After complete conversion of starting material, the reaction mass was filtered. The filtrate was evaporated to yield SAXAGLIPTIN free base of formula-I as a foamy solid. To the solid ethyl acetate (5 ml), 20 micro liters of water and n-hexane (20 ml) were added, the mixture stirred at 0-5° C. and the white solid formed was filtered to yield 7.06 gm (95%) of SAXAGLIPTIN MONO HYDRATE of formula-XII. The solid obtained was dissolved in ethyl acetate (30 ml), 2.15 ml of concentrated hydrochloric acid added at 20-25° C., stirred for one hour and the white solid formed was filtered to yield saxagliptin dihydrate mono-hydrochloride of formula-II.

EXAMPLE-8

Preparation of (2S)-2-{[(benzyloxy)carbonyl]amino}-2-(3-hydroxyadamantan-1-yl) acetic acid (formula-XIV)

The (2S)-2-amino-2-(3-hydroxyadamantan-1-yl)acetic acid hydrochloride (20 g) was dissolved in 100 ml water at 25-30° C. The pH of the solution was adjusted to 8.5-9.5 with aqueous sodium hydroxide solution at 5° C. To the mixture benzyl chloroformate (10.7 g) was added and set aside for 4 h at 25-30° C. The reaction mass was washed with MTBE (25 ml) and the pH of the aqueous phase adjusted to 2-3 with dilute hydrochloric acid. Aqueous phase was extracted with ethyl acetate, the organic phase dried and evaporated to yield 26 g (95%) of the title product. M.P 55-58° C., H$^1$NMR (300 MHz, CDCl$_3$): 1.39-1.58 (m, 12H), 2.04-2.07 (s, 2H), 3.86-3.89 (dd, 1H), 4.98 (s, 2H), 5.11 (s, 1H), 7.0 (d, 1H), 7.16-7.27 (m, 5H).

We claim:
1. A process for the preparation of (1S,3S,5S)-2-[2(S)-2-amino-2-(3-hydroxy-1-adamantan-1-yl)acetyl]-2-azabicyclo[3.1.0]hexane-3-carbonitrile of Formula-I, which comprises the debenzylation of benzyl N-[(1S)-2-[(1S,3S,5S)-3-cyano-2-azabicyclo[3.1.0]hexan-2-yl]-1-(3-hydroxyadamantan-1-yl)-2-oxoethyl] carbamate of Formula-XI, by dissolving in a suitable solvent and reacting with a hydrogen source in the presence of a metal catalyst

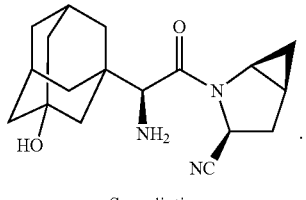

Formula-I

Saxagliptin

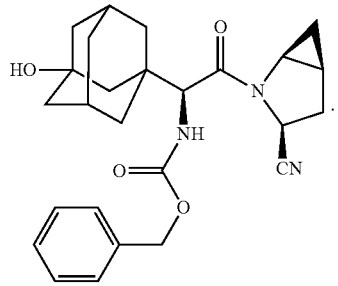

Formula-XI

2. The process of claim 1 wherein the metal catalyst is palladium on carbon (Pd/C) and the hydrogen source is from the group consisting of hydrogen gas, ammonium formate, ammonium acetate, ammonium chloride and formic acid.

3. The process of claim 1 wherein suitable solvent is selected from the group consisting of acetonitrile, methanol, ethanol, and 2-propanol.

4. The process of claim 1 wherein the reaction is carried out at a temperature of about 0° C. to 50° C.

5. The process of claim 1 wherein the reaction is carried out at a temperature of about 15-30° C.

6. A compound (2S)-2-{[(benzyloxy)carbonyl]amino}-2-(3-hydroxyadamantan-1-yl)acetic acid (Formula-XIV)

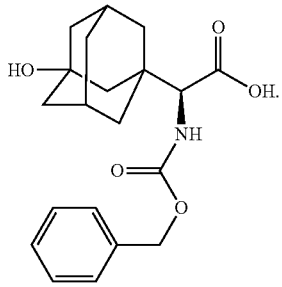

Formula-XIV

7. A compound benzyl N-[(1S)-2-[(1S,3S,5S)-3-carbamoyl-2-azabicyclo[3.1.0]hexan-2-yl]-1-(3-hydroxyadamantan-1-yl)-2-oxo-ethyl]carbamate (Formula-XV)

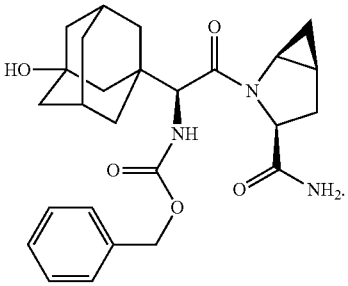

Formula-XV

8. A compound benzyl N-[(1S)-2-[(1S,3S,5S)-3-cyano-2-azabicyclo[3.1.0]hexan-2-yl]-1-(3-hydroxyadamantan-1-yl)-2-oxo-ethyl]carbamate (Formula-XI)
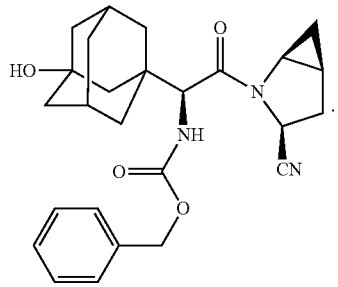
Formula-XI
* * * * *